(12) United States Patent
Gries

(10) Patent No.: US 8,511,214 B2
(45) Date of Patent: Aug. 20, 2013

(54) TUBULAR STRUCTURE AND METHOD FOR MAKING THE SAME

(75) Inventor: Sara Jane Gries, Plymouth, MN (US)

(73) Assignee: AGA Medical Corporation, Plymouth, MN (US)

(*) Notice: Subject to any disclaimer, the term of this patent is extended or adjusted under 35 U.S.C. 154(b) by 0 days.

(21) Appl. No.: 13/091,763

(22) Filed: Apr. 21, 2011

(65) Prior Publication Data

US 2012/0271403 A1 Oct. 25, 2012

(51) Int. Cl.
*D04C 3/00* (2006.01)

(52) U.S. Cl.
USPC .............................................. 87/34

(58) Field of Classification Search
USPC ....................... 87/1, 8, 9, 11, 13, 34
See application file for complete search history.

(56) References Cited

U.S. PATENT DOCUMENTS

| | | | |
|---|---|---|---|
| 1,188,741 A * | 6/1916 | Dunkerley | 87/30 |
| 3,748,952 A | 7/1973 | Petzetakis | |
| 4,158,984 A | 6/1979 | Griffiths | |
| 4,275,638 A | 6/1981 | DeYoung | |
| 4,494,436 A * | 1/1985 | Kruesi | 87/23 |
| 4,519,290 A | 5/1985 | Inman et al. | |
| 4,753,149 A | 6/1988 | Celani | |
| 5,061,275 A | 10/1991 | Wallsten et al. | |
| 5,099,744 A | 3/1992 | Hurst et al. | |
| 5,203,249 A | 4/1993 | Adams et al. | |
| 5,388,497 A * | 2/1995 | Akiyama et al. | 87/34 |
| 5,398,586 A * | 3/1995 | Akiyama et al. | 87/6 |
| 5,554,181 A | 9/1996 | Das | |
| 5,979,288 A * | 11/1999 | Gallagher et al. | 87/36 |
| 6,360,644 B1 | 3/2002 | Bettger et al. | |
| 6,447,531 B1 | 9/2002 | Amplatz | |
| 6,579,815 B1 | 6/2003 | Popper et al. | |
| 6,613,078 B1 | 9/2003 | Barone | |
| 7,093,527 B2 | 8/2006 | Rapaport et al. | |
| 7,793,576 B2 * | 9/2010 | Head et al. | 87/34 |
| 2006/0060325 A1 | 3/2006 | Gordon et al. | |
| 2007/0168018 A1 | 7/2007 | Amplatz et al. | |
| 2008/0187699 A1 * | 8/2008 | Sijpkes et al. | 428/36.3 |
| 2008/0229921 A1 * | 9/2008 | Head et al. | 87/20 |
| 2009/0005847 A1 | 1/2009 | Adams | |
| 2010/0052203 A1 * | 3/2010 | Inazawa et al. | 264/103 |
| 2010/0298952 A1 | 11/2010 | Busold et al. | |

OTHER PUBLICATIONS

International Search Report and Written Opinion from International Application No. PCT/US12/33919, mailed Sep. 6, 2012.

* cited by examiner

*Primary Examiner* — Shaun R Hurley
(74) *Attorney, Agent, or Firm* — Alston & Bird LLP

(57) ABSTRACT

A tubular structure and method for making a tubular structure are provided, where the tubular structure includes at least one layer of braided strands. In general, at least one portion of the braided strands exhibits a braid pattern of crests and troughs (e.g., a wave pattern, which may include sinusoidal, square, and/or sawtooth waves) along a length of the tubular structure. The wave pattern can be created by rotating the mandrel onto which the tubular structure is braided during the braiding process, such as by angularly oscillating the mandrel about its longitudinal axis or about its transverse axis. As a result, the tubular structures may have increased radial strength, collapse resistance, torque transmission, column strength, and kink resistance. The tubular structures may be used in medical devices, such as stent-grafts, as well as in other medical and non-medical devices, such as in hoses, tubing, filters, and other devices.

35 Claims, 12 Drawing Sheets

TUBULAR STRUCTURE AND METHOD FOR MAKING THE SAME

BACKGROUND

I. Field of the Invention

Embodiments of the present invention relate generally to braiding of filaments for use in medical devices and non-medical applications and, more particularly, to a tubular structure and methods for braiding patterns that promote radial strength, collapse resistance, torque transmission, column strength, and kink resistance.

II. Description of the Related Art:

Braiding machines have long been used in industry for braiding a variety of filaments, including fibers, thread, yarn, wire, and polymer strands, into tubular structures, such as for use as coverings (e.g., on electric wire) to provide insulation, abrasion resistance and thermal protection. In addition, tubular structures have been used to impart other characteristics, such as radial support (e.g., for high pressure hoses), collapse resistance (e.g., for vacuum tubing), kink resistance, and column strength (e.g., for tubing) and for enhancing other torque transmission properties for various applications.

In the medical device industry, for example, filament braiding has been incorporated into products such as balloon catheters, stents, occlusion devices, vascular grafts, and guide and diagnostic catheters. In particular, tubular structures having a small diameter and incorporating stainless steel, Nickel Titanium (NiTi) alloys, known in the art as Nitinol, and other metallic alloys have been used as coverings, incorporated into a tubular wall, or used as stand-alone medical devices. For example, the use of braided Nitinol alloy wire or certain other alloys exhibiting shape memory characteristics has allowed many devices to be fabricated that can be collapsed for delivery into the body through a catheter and, once deployed from the catheter, can self-expand to a predetermined shape.

In applications such as the delivery of medical devices into remote portions of the human vasculature, the tubular structures should be capable of passing through small diameter vasculature. Thus, the wall thickness and overall profile of the devices becomes increasingly important to the success of the procedure and the comfort of the patient. At the same time, it is desirable for such tubular structures to possess sufficient strength to accomplish certain tasks. For example, tubular structures may be used in stents for the medical treatment of vascular disease to hold open arterial segments that have been narrowed by plaque build up. In some cases, such as with braided Nitinol stents, the stent is stretched to draw down the diameter for delivery through a catheter and self-expands when released from the catheter to abut the arterial wall for supporting the diseased segment. It is thus important that stents have sufficient radial force to hold the artery segment open and resist collapse and kinking, while still being flexible enough to be passed through the delivery catheter through arterial bends without increasing the wire diameter or compromising the functionality of the stent. Similar considerations may also apply to catheter tubing and other tubular structures.

Accordingly, for medical and other applications, there is a need for improved tubular structures that provide increased radial strength, kink resistance, and column strength without necessarily increasing wall thickness in a manner that is simple, cost effective, and overcomes the shortcomings of conventional solutions.

SUMMARY OF THE INVENTION

Embodiments therefore provide a tubular structure and method for making a tubular structure, where the tubular structure includes at least one layer of braided strands. In general, at least one section of the braided strands exhibits a braid pattern of crests and troughs (e.g., a wave pattern) along a longitudinal axis of the tubular structure. The wave pattern is created by rotating the mandrel onto which the tubular structure is braided during the braiding process, such as by angularly oscillating the mandrel about its longitudinal axis or about a transverse axis (e.g., rotating the mandrel in opposite directions with respect to a neutral position). As a result, the tubular structures may have increased radial strength, collapse resistance, torque transmission, column strength, and/or kink resistance as compared to tubular structures formed using a conventional braiding process without mandrel rotation.

In one embodiment, a method of braiding a plurality of strands into a tubular structure is provided. A first set of strands and a second set of strands are braided onto a mandrel, and the mandrel is moved along a longitudinal axis of the mandrel as the first and second sets of strands are being braided. The mandrel is additionally rotated as the first and second sets of strands are being braided onto the mandrel. The mandrel may be rotated about the longitudinal axis or about a transverse axis. Rotation of the mandrel may result in at least a portion of the braided strands exhibiting a wave pattern that includes crests and troughs along a length of the tubular structure.

Braiding the first and second sets of strands onto the mandrel may include rotating the first set of strands in a first direction about the axis and rotating the second set of strands in a second direction about the axis. In some cases, each strand extends from a spool to the mandrel, and braiding the first and second sets of strands onto the mandrel may include rotating the spools of the first set of strands in a first direction about the axis, rotating the spools of the second set of strands in a second direction about the axis, and translating the spools of the first set of strands and the spools of the second set of strands radially with respect to the axis.

In some cases, the speed of the braiding of the first and second sets of strands or the speed of movement of the mandrel along the axis may be changed as the first and second sets of strands are being braided onto the mandrel to vary a pic count (number of strand crossover points per unit length) of a resulting braid pattern. Furthermore, a first braid pattern may be applied to a first portion of the tubular structure, and a second braid pattern may be applied to a second portion of the tubular structure, the first braid pattern being different from the second braid pattern. At least one of the first and second braid patterns may be a wave pattern.

The braid pattern of the tubular structure may be stabilized in various ways. For example, the braid pattern may be heat set. Alternatively or additionally, the first and second sets of strands may be braided onto at least one polymer layer. In some cases, a covering may be applied to an exterior surface of at least a portion of the tubular structure.

In some embodiments, the mandrel may be angularly oscillated, and a speed of the angular oscillation may be changed. In some instances, a maximum angle through which the mandrel rotates may be varied. Varying the maximum angle may include rotating the mandrel to a first maximum angle in a first direction and rotating the mandrel to a second maximum angle in a second direction, where the magnitude of the second maximum angle is different from the magnitude of the first maximum angle. In some cases, the step of braiding the first and second sets of strands may include braiding the first and second sets of strands onto the mandrel in multiple layers.

In other embodiments, a tubular structure is provided that includes at least one layer of braided strands. At least a portion of the braided strands exhibits a wave pattern that includes crests and troughs along a length of the tubular structure. In some cases, the wave pattern may include a sinusoidal wave, a square wave, and/or a sawtooth wave.

In some embodiments, the tubular structure may include at least one polymer layer. A covering may be applied to a surface of the braided strands in some cases. The braided strands may exhibit a first wave pattern in one portion of the tubular structure and a second wave pattern in another portion of the tubular structure, and the first wave pattern may be different from the second wave pattern. Furthermore, the tubular structure may include multiple layers of braided strands.

At least some of the strands may include metal, polymer, natural material, and/or combinations of the same. In addition, at least some of the strands may include at least one metal selected from the group consisting of steel, stainless steel, shape memory alloy, and elastic alloy. In some cases, at least some of the strands may include a shape memory alloy, such that the resulting tubular structure may be configured to have an expanded configuration when the tubular structure is not constrained and to have a collapsed configuration when the tubular structure is constrained. In this way, the tubular structure may be configured to self-expand from the collapsed configuration to the expanded configuration when a constraint is removed. At least some of the strands may include Nickel Titanium (NiTi) alloy.

In still other embodiments, a medical device is provided that is configured to treat a target site within a patient's body. The medical device may comprise a tubular structure, and the tubular structure may comprise a plurality of braided strands exhibiting a wave pattern that includes crests and troughs along a length of the tubular structure.

The tubular structure may comprise a covering applied to a surface of the braided strands. In some cases, the braided strands of the tubular structure exhibit a first wave pattern in one portion of the tubular structure and a second wave pattern in another portion of the tubular structure, wherein the first wave pattern is different from the second wave pattern. Also, the tubular structure may include multiple layers of braided strands.

In some cases, at least some of the strands of the tubular structure may comprise at least one metal selected from the group consisting of steel, stainless steel, shape memory alloy, and/or elastic alloy. Furthermore, at least some of the strands of the tubular structure may comprise a shape memory alloy such that at least a portion of the medical device is configured to have an expanded configuration when the device is not constrained and to have a collapsed configuration when the device is constrained. Thus, the medical device may be configured to self-expand from the collapsed configuration to the expanded configuration when a constraint is removed

BRIEF DESCRIPTION OF THE DRAWINGS

The foregoing features and advantages of the invention will become apparent to those skilled in the art from the following detailed description of a preferred embodiment, especially when considered in conjunction with the accompanying drawings in which like numerals in the several views refer to corresponding parts.

DETAILED DESCRIPTION

Figure 1:
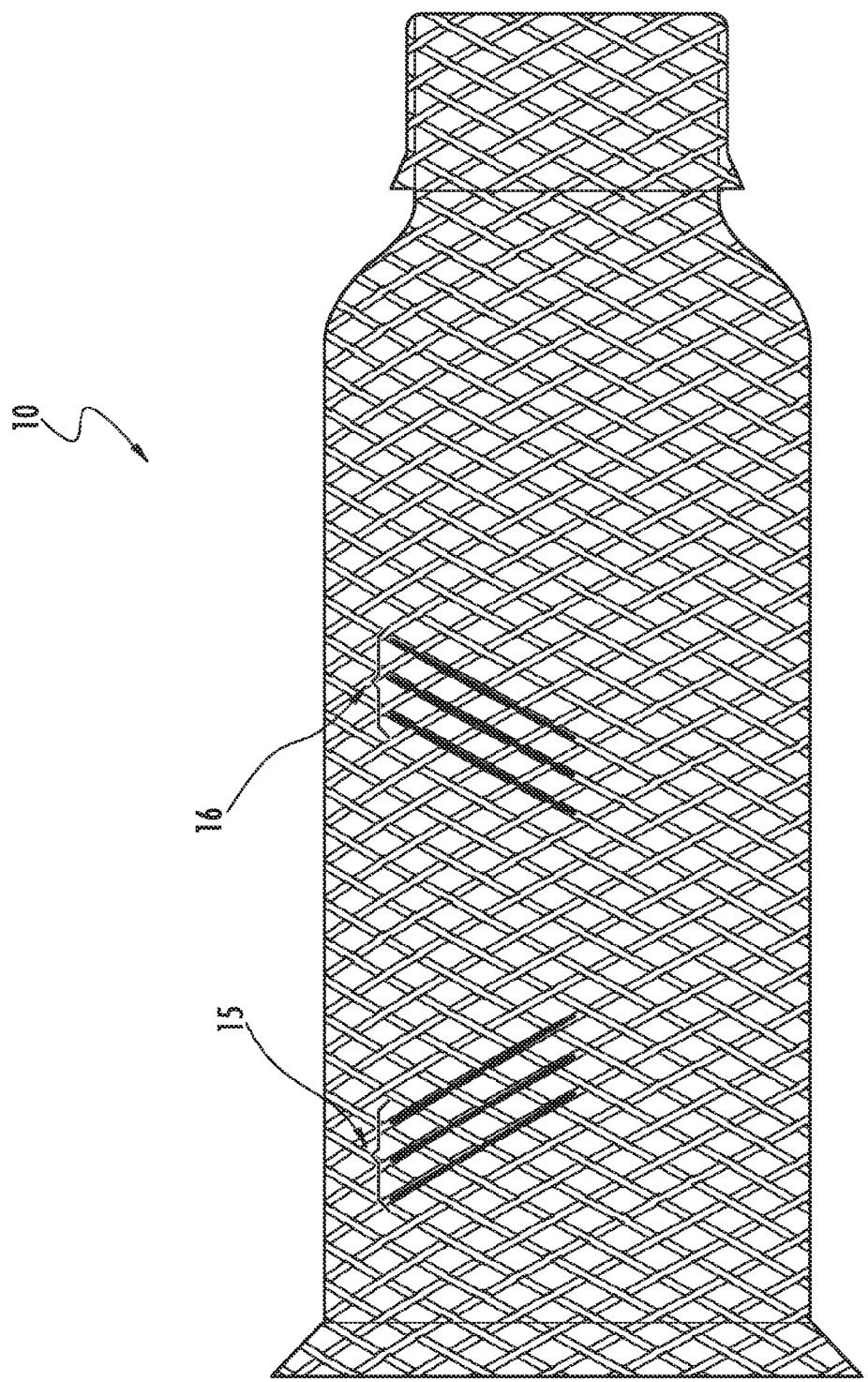
FIG. 1 is an illustration of a stent-graft having a braided wire tubular structure according to an exemplary embodiment.

Embodiments of the present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Embodiments provide a tubular structure and method for making a tubular structure that includes at least one layer of braided strands. In general, at least one portion of the braided strands exhibits a braid pattern of crests and troughs (e.g., a wave pattern) as observed along a length of the tubular structure. The wave pattern may be created by rotating the mandrel onto which the tubular structure is braided during the braiding process, such as by angularly oscillating the mandrel about its longitudinal axis. Alternatively, the wave pattern may be created by rotating the mandrel about a transverse axis (i.e., pivoting the mandrel), raising and lowering the whole mandrel, rotating the braiding machine with respect to the longitudinal axis, or changing the speed of carrier rotation while maintaining the speed of the mandrel's axial movement, as described in greater detail below.

The observed wave pattern may be the pathway of strand cross-over points that is created by the angular oscillations or alternative movements of the mandrel and/or the braiding machine. As a result, according to embodiments of the present invention, the tubular structures may have increased radial strength, collapse resistance, torque transmission, column strength, and/or kink resistance as compared to tubular structures formed using conventional braiding processes.

While the following embodiments of the present invention include descriptions with respect to a tubular structure for use in medical device applications, it will be understood by persons skilled in the art that the present embodiments are not limited to use in medical devices and that the tubular structures and methods described may have use in other industrial applications, as well. Thus, although the use of tubular structures exhibiting a wave braid pattern that includes crests and troughs are described below for use in medical devices, wave patterns in braided tubular structures may be useful in various types of devices, medical and otherwise, including air pressure lines, vacuum tubing, hydraulic lines, fire hoses, carbon fiber braiding, filtering applications, and/or spiral wrap filters, where portions of the filter trap small particles locally while adjacent areas allow fluid to pass to the next layer of the filter. For example, tubular structures exhibiting a wave braid pattern with crests and troughs, in some cases, may be useful for mixing fluids. The mixing of fluids may be enhanced, for example, due to the turbulence generated by fluid flow through a braided wave configuration (as opposed to a conventional linear braid configuration).

Embodiments of the method of braiding described herein may be used for braiding a variety of filamentary materials. These filamentary materials may include, for example, fibers, thread, yarn, cable, metallic wires, polymer strands, and combinations of these materials, any of which are referenced herein as "strands," and such terms may be used interchangeably.

As an example, the tubular structures described herein may be useful as medical devices. One type of medical device that may include a tubular structure is a stent-graft 10 (depicted in FIG. 1) used in treating a target site within the body, e.g., for excluding various vascular abnormalities, such as an aneurysm. The stent-graft 10 may include a fabric portion combined and affixed with a stent portion. The fabric portion may be inside, outside, or both inside and outside the stent portion and may serve to channel blood flow through the vessel, while the stent portion may provide the radial expansion force to anchor the stent-graft against the vessel wall on either side of the aneurysm and to provide a stable luminal diameter as the stent-graft bridges the aneurysm.

Other types of medical devices may include balloon catheters, stents, occlusion devices, guide and diagnostic catheters, flow restrictors, shunts, filters, and other types of devices for placement in the vascular system (e.g., the cardiovascular system) for treating a target site. It is understood that the use of the term "target site" is not meant to be limiting, as the device may be configured to treat any target site, such as an abnormality, a vessel, an organ, an opening, a chamber, a channel, a hole, a cavity, or the like, located anywhere in the body. For example, the abnormality could be any abnormality that affects the shape or the function of the native lumen, such as an aneurysm, a lesion, a vessel dissection, a flow abnormality, or a tumor. Furthermore, the term "lumen" is also not meant to be limiting, as the abnormality may reside in a variety of locations within the vasculature, such as a vessel, an artery, a vein, a passageway, an organ, a cavity, or the like.

In such applications, the medical device is often required to pass through small diameter arteries and other body structures. For example, in some embodiments, the braided tubular structure is configured to be elongated and radially collapsed for delivery through a catheter. The tubular structure may then be released from the catheter at the target site within the vasculature. There, the stent-graft may self-expand to abut the native vessel wall on either side of, for example, an aneurysm. Thus, after deployment, the stent-graft portion within the aneurysmal section will have expanded to its predetermined memorized diameter, which bridges the aneurysm and creates a vascular conduit.

In some cases, it may be desirable for a portion of the stent-graft to have increased radial strength at those locations on either side of the location (for example, the aneurysm) where the stent or stent-graft is anchored to the native vessel wall. It may also be desirable for the stent-graft to resist diameter expansion from blood pressure (e.g., in the aneurysmal section), for example so as not to place pressure on the thin wall of the aneurysm. This could be accomplished by larger diameter strands; however, larger diameter strands may increase the device profile, which may require a larger diameter delivery catheter, which may in turn limit the treatment of some patients having smaller vessels or cause patient trauma during delivery of the device through vessels narrowed by plaque and/or as a result of using a larger introducer sheath or using a groin cut down procedure to access the vessel.

Thus, embodiments of the tubular structure described herein provide for desired performance attributes while enabling a thinner tubular wall thickness or, alternatively, allowing for smaller inside or outside tubular diameters. In addition, for a given strand diameter and, thus, a given wall thickness, improved properties may be obtained for a tubular structure. These benefits allow for the use of smaller diameter devices or improved performance parameters for the tubular structure used. As a result, patient trauma may be reduced and/or more patients may be able to receive treatment. In accordance with certain embodiments, for example, the wall thickness of medical devices that include tubular structures braided as described in greater detail below is approximately 0.002 inches to approximately 0.030 inches, but varies considerably based on the type of product, anatomic limitations, and the intended use of the device.

In addition, the embodiments described below provide tubular structures that can be formed via a continuous braiding process, where the tubular structure has radial strength properties that may vary along the length of the tubular structure or other improved properties such as collapse resistance, torque transmission, column strength, and/or kink resistance, as desired. The tubular braided structure may be used to form various medical devices such as, for example, a bell shape occluder designed for the closure of the Patent Ductus Arteriosus (PDA). In this case, the tubular braided structure may be shaped in or around a bell-shaped mold and may be heat treated while held in the mold to impart memory of this shape into the design. The braided strand ends of the device may be clamped or otherwise held together to prevent unraveling of the braid. The device may then be stretched axially to reduce its profile so that it may be delivered into the vasculature through a delivery catheter, as described above. At a target site within a vessel, the device may be released from the catheter to self-expand into the preset bell shape. A portion of the device that anchors against the vessel wall may require a certain radial strength, whereas a flanged portion of the bell shape may not require the same radial strength. Thus, in accordance with the embodiments described below, the radial strength of a select portion of the device may be increased without increasing the strand diameter, and/or adequate vessel wall anchoring (e.g., radial stiffness) may be achieved while fabricating the device from smaller diameter strands, thereby reducing the device's collapsed profile for delivery through a smaller catheter.

In some cases, the tubular structure may include one or more layers of occlusive material. For example, the layers of occlusive material may be independent tubular members that are layered concentrically with respect to one another. The layers may be elongated to a reduced-diameter configuration for delivery to a target site and may expand upon deployment as explained in further detail below. In other cases, the plurality of layers may be folded with respect to one another into a layered structure. According to one aspect, the folded layers may be configured to be separated into a non-overlapping configuration for delivery within a catheter and return to the overlapping configuration when deployed from the catheter. In the preset, overlapping configuration, the occlusive material may be configured to provide a central passageway or lumen for fluid flow therethrough (e.g., blood flow through the stent-graft).

In the case of a medical device, such as the stent-graft 10 shown in FIG. 1, the device may comprise a plurality of layers of occlusive material such that the device may have a variety of occluding materials capable of at least partially inhibiting blood flow therethrough to facilitate the formation of thrombus and endotheliazation around the device. As used herein, "substantially preclude or impede flow" shall mean, functionally, that blood flow may occur for a short time, e.g., about 3-60 minutes through the occlusive material, but that the body's clotting mechanism or protein or other body deposits on the braided wire strands results in occlusion or flow stoppage after this initial time period. For instance, occlusion may be clinically represented by injecting a contrast media into the upstream lumen of the device and, if no contrast media flows through the wall of the device after a predetermined period of time as viewed by fluoroscopy, the position and occlusion of the device is adequate. Moreover, occlusion of the target site could be assessed using various ultrasound echo Doppler modalities.

In one embodiment, the tubular structure includes at least one layer of braided strands, the strands, for example, having a predetermined relative orientation with respect to one another. The occlusive material of the device, such as the stent-graft 10, may be a metal fabric including a plurality of strands, such as two sets 15, 16 of essentially parallel generally helical strands, with the strands of one set having a "hand," i.e., a direction of rotation, opposite that of the other set, as illustrated in FIG. 1. Although the term "braided" is used herein to describe the combination of strands to form the tubular structure, it will be understood by those skilled in the art that the strands may be braided, interwoven, knitted, or otherwise combined to define a fabric, and such terms may be used interchangeably.

In some embodiments, the tubular structure is described as having a braid pattern. The phrase "braid pattern" is used herein to describe a series of repeating elements that form a pattern resulting from a combination of strands that may be perceived, for example, along a length of the tubular structure. The braid pattern may be the result of the perceived path of strand cross-over points, rather than the path of an individual strand or set of strands. For example, in some embodiments detailed below, at least a portion of the braided strands exhibits a wave pattern, where the repeating element is a wave (e.g., as illustrated in FIGS. 9-13). The repeating elements may or may not be identical. In other words, where the repeating element is a wave, the amplitude and/or frequency of the wave may not be the same across all the waves. For example, the wave pattern in some cases may be a series of waves of increasing or decreasing amplitude, or increasing or decreasing frequency, as described below.

Figure 2A:
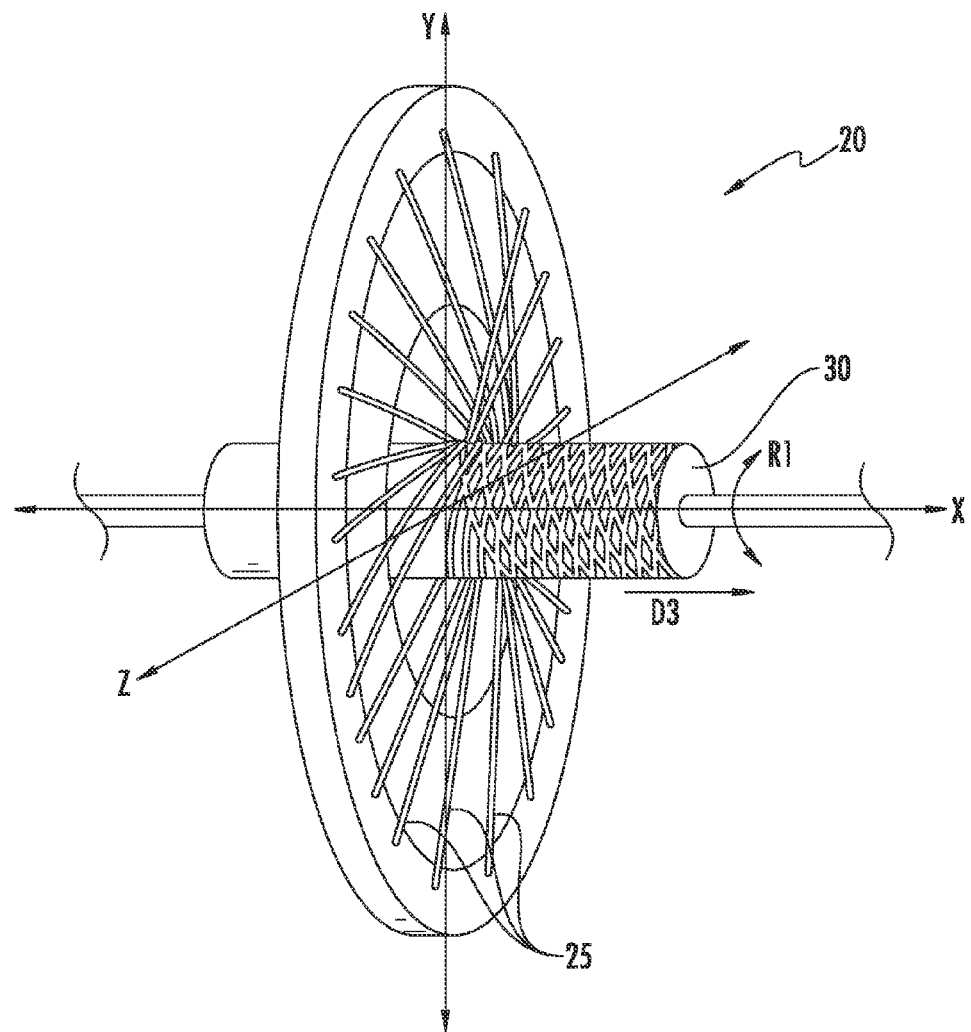
FIG. 2A is an illustration of a portion of a braiding machine for braiding strands onto a mandrel according to an exemplary embodiment.
Figure 2B:
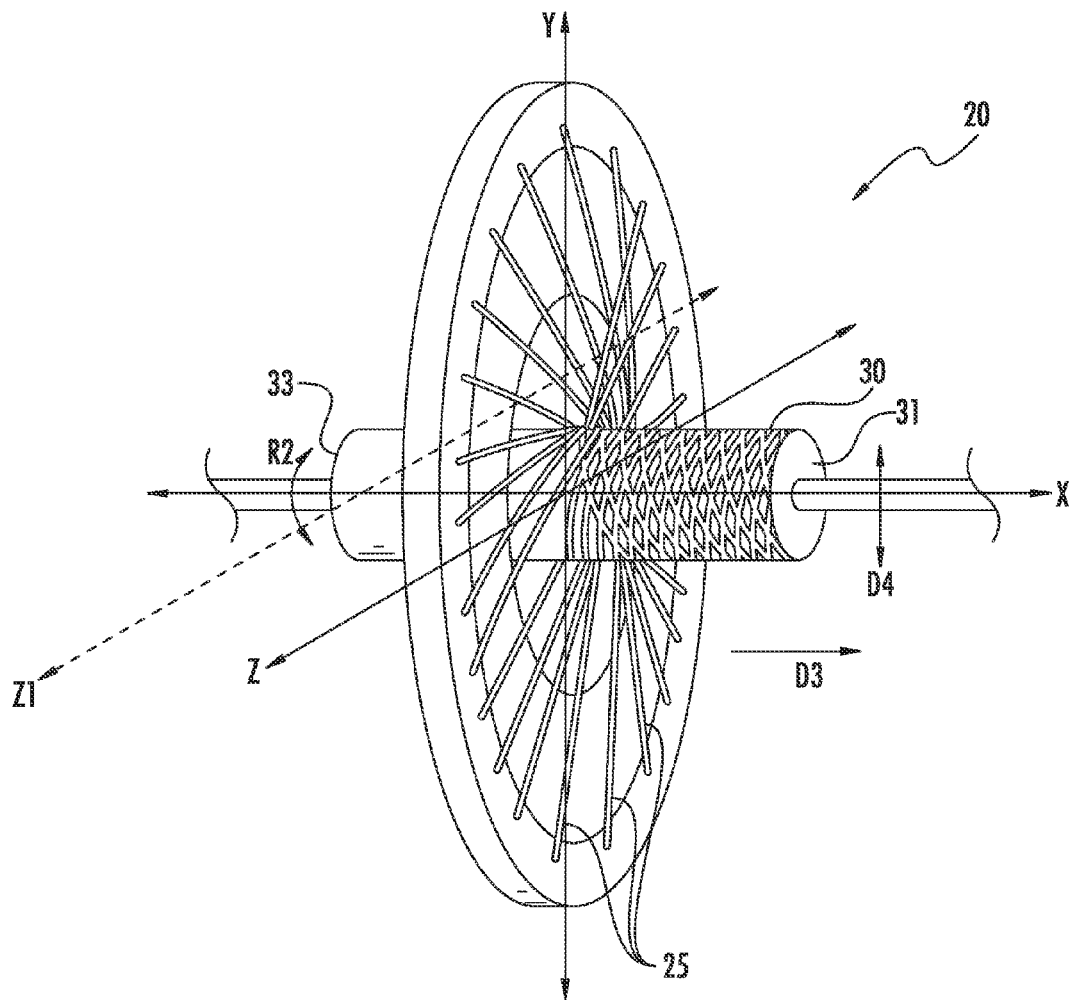
FIG. 2B is an illustration of a portion of a braiding machine for braiding strands onto a mandrel according to another exemplary embodiment.
Figure 3:
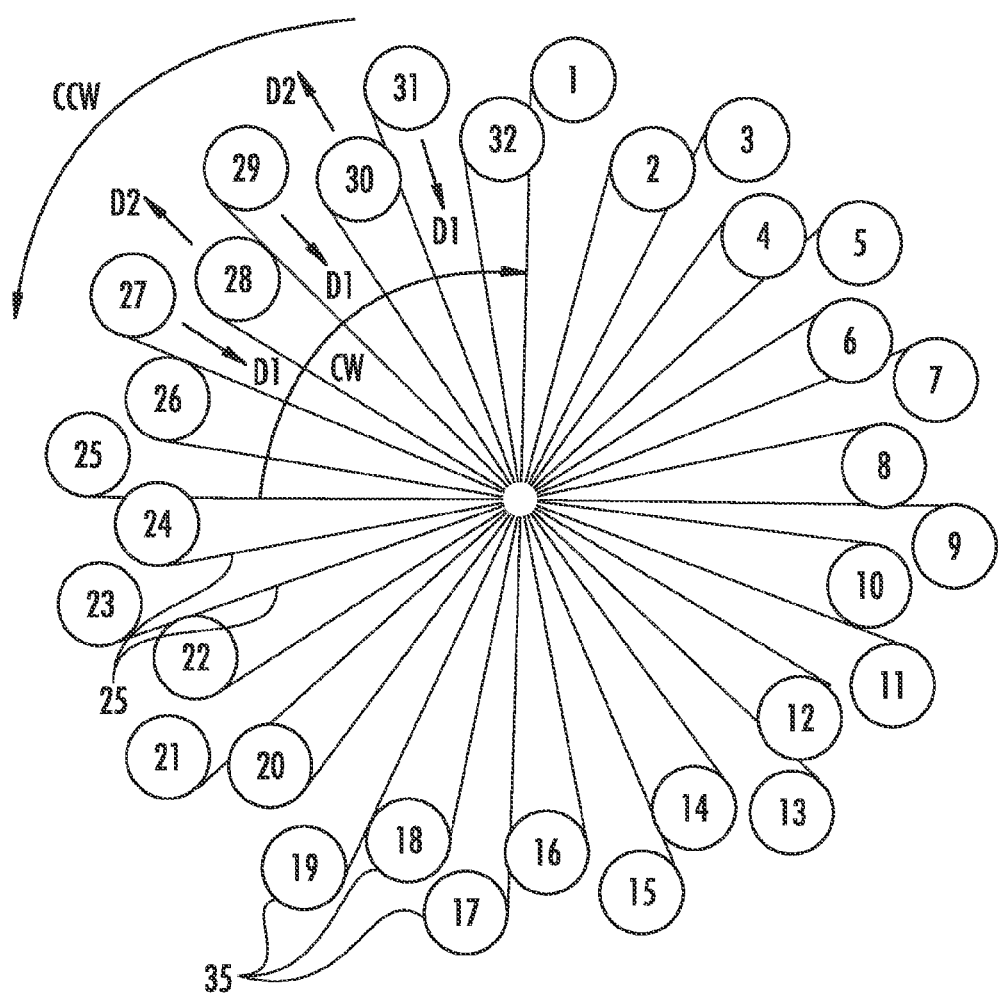
FIG. 3 is an illustration of the movement of spool carriers for braiding a tubular structure according to an exemplary embodiment.

In general, embodiments of the tubular structures may be formed using a braiding machine 20, which interweaves sets of strands 25 onto a mandrel 30, as illustrated in FIGS. 2A and 2B. With reference to FIG. 3, for example, rotating spool carriers 35 may be provided, where each spool carrier is configured to carry at least one spool of the strands 25. In some cases, however, one or more spool carriers may be left intentionally empty, or a carrier may hold one or more spools according to the particular braid pattern desired. In FIGS. 2A, 2B, and 3, the braiding machine 20 is shown as holding 32 spool carriers 35 (numbered 1-32); however, any number of spool carriers may be used according to the specific configuration of the machine, the desired characteristics of the resulting tubular structure, and/or the user's preferences, as described in greater detail below.

Exemplary braiding machines may be adapted to perform the processes described herein. These machines may be modified to provide a number of variable braid patterns and to handle different strand materials and numbers of strands. Braiding machines used in accordance with the embodiments described herein may include multiple carriers of strands. They may be configured to braid, for example, fine wire and textile strands using 8-288 filament carriers.

The individual carriers 35 shown in FIG. 3 are divided into two sets of strands, and each strand extends from a respective spool to the mandrel 30. In some cases, however, more than two sets of strands may be used, such as 3 or 4 sets of strands, depending on the desired braid pattern. In FIG. 3, the spools of each set are arranged circumferentially about a longitudinal axis X of the mandrel 30 (i.e., the axis of braid formation), with the spools carrying the first set of strands rotating in a generally circular manner in a first direction about the axis X and the spools carrying the second set of strands rotating in a generally circular manner in a second direction about the axis. Thus, the first and second sets rotate in opposite directions within a plane YZ that is generally perpendicular to the longitudinal axis X. For example, the spools of one set of strands 25 (e.g., the even-numbered spool carriers 35 shown in FIG. 3) may move in the clockwise direction CW, and the spools of the second set of strands (e.g., the strands corresponding to the odd-numbered spool carriers shown in FIG. 3) may move in a counter-clockwise direction CCW, as illustrated.

In an exemplary embodiment, the strands are pulled in a direction that is at an angle to and away from the plane YZ of the spool carriers (shown in FIGS. 2A and 2B). The resulting tubular structure thus comprises braided strands that traverse the circumference of the mandrel, with the resulting wave pattern in some cases appearing to be aligned substantially straight along the axis X defined by the mandrel 30, as described in greater detail below.

According to one embodiment, as the spool carriers 35 travel in circular paths about the axis X, they are also translated radially with respect to the axis X. In other words, the radius of travel of the spools about the axis X is changed as each spool moves in a direction D1, D2 towards or away from the axis X, passing inside of one spool carrier 35 and outside of the next spool carrier. This action forms a tubular structure about the mandrel 30 with strands 25 that are woven over and under each other in a braided configuration.

Figure 4:
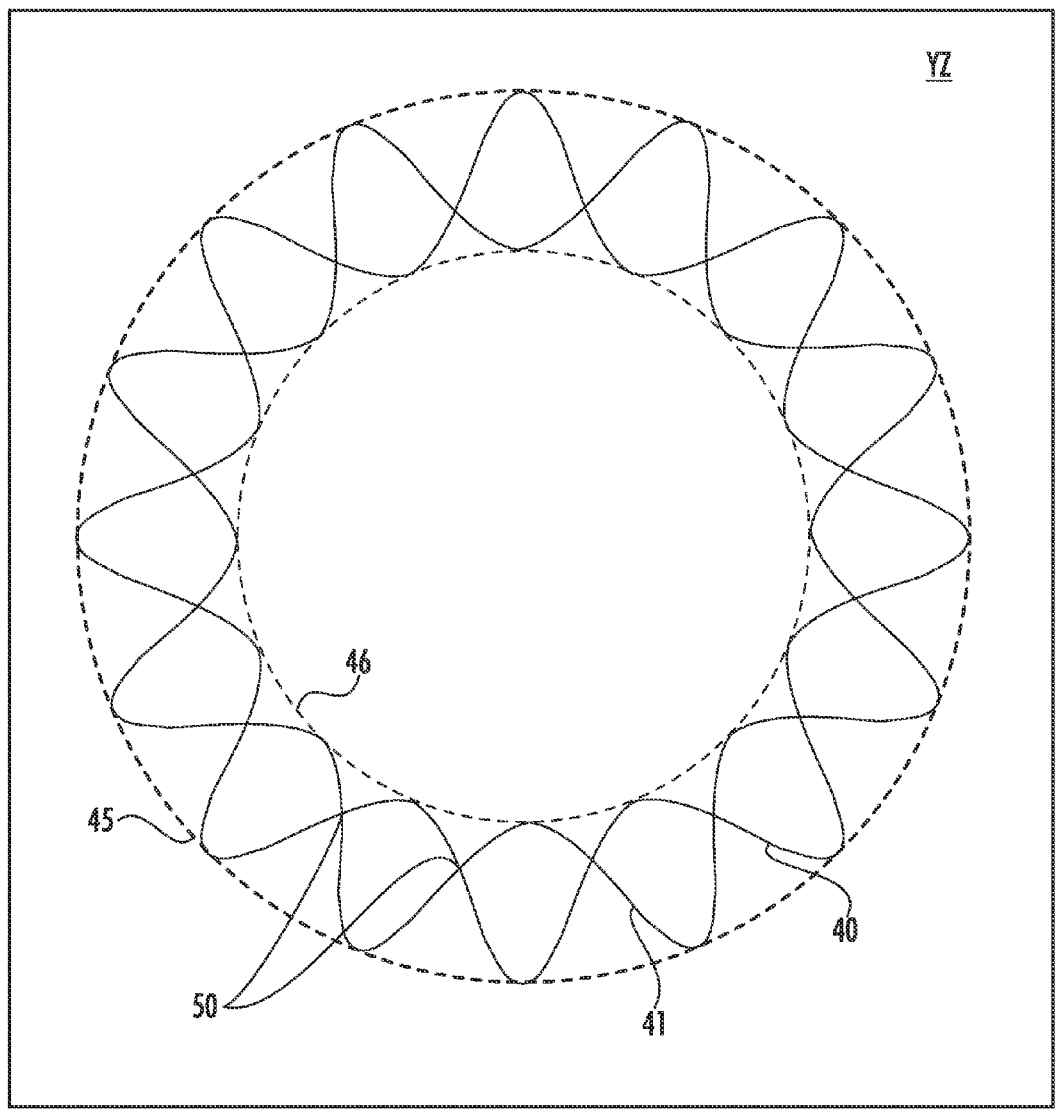
FIG. 4 is an illustration of the paths of movement of spools of first and second sets of strands according to an exemplary embodiment.

According to one embodiment, as illustrated in FIG. 4, the individual carriers of the first set of strands may move in a first serpentine pattern 40 between an outer circumference of rotation 45 and an inner circumference of rotation 46 within the plane of rotation YZ. The carriers of the second set of strands may move in a similar second serpentine pattern 41 that is 180° out of phase with the first serpentine pattern 40 with resultant cross-over points 50. A secondary mechanism allows the carriers 35 of each set to pass by each other in a controlled manner without collision, thereby coordinating the rotation and translation of the carriers about the axis X.

In addition to the movement of the spools, the braid mandrel 30 may also be moved along the axis X as the first and second sets of strands 25 are being braided onto the mandrel. For example, as shown in FIGS. 2A and 2B, the mandrel 30 may be moved in the direction D3 as the strands 25 are being braided onto the mandrel to form a layer of the tubular structure. The mandrel 30 may be advanced in the direction D3 axially along the axis X, generally perpendicularly to the carrier rotation plane YZ, and the speed at which the carriers move may define the rate of braid formation. Thus, as the carriers 35 rotate and translate and the strands 25 pass over and under one another to braid the strands, the axial movement of the mandrel 30 allows the braided strands to be wrapped into a tubular configuration. The speed of axial movement of the mandrel 30 may be altered in relation to the rate of carrier movement as desired to change the pic count or to change the angle of the braid, as described below.

In some embodiments, a second layer may be braided on top of an existing braided layer, e.g., using the first braided layer as the mandrel, in a similar manner as that by which the first layer was braided. It may be easier, however, to braid the second layer independently of the first layer and subsequently place the second layer coaxially over the first layer in a separate operation. In some cases, both the first and second layers may be braided to include a wave pattern. In other cases, however, only one of the layers may exhibit the wave pattern. For example, the first (e.g., inner) layer may be braided to include a wave pattern, whereas the second (outer) layer may not include any wave pattern. The resulting tubular structure may thus exhibit a smooth exterior surface in some cases.

Depending on the configuration of the braiding machine 20, many different braid patterns may be formed. For example, in one braid pattern, a single strand 25, if followed, may pass over one strand of the opposite helix wind (the opposite "hand"), under the next strand of opposite helical wind, over the next strand of the opposite helix wind, etc., in a repeating pattern. As another example, one or more strands of one hand can also pass over one or more strands of the opposite hand and then under one or more strands of the opposite hand in a repeating pattern.

In addition, as noted above, the rotational speed of the spools and the speed at which the mandrel 30 is moved along the axis X may be adjusted according to the particular application and/or user preferences to set a pic count of the resulting braid pattern. The pic count can be increased by increasing the number of strands braided or by slowing the axial speed of the mandrel in the direction D3. In some embodiments, such as for stent-graft applications, the pic count may range from 52 to 78 PPI (pics per inch), although a higher or lower pic count may be used depending on the desired characteristics to be imparted to the tubular structure. Thus, the speed of the movement of the mandrel 30 along the axis X as the first and second sets of strands are being braided onto the mandrel may be changed to vary the pic count of the resulting braid pattern, as desired. As noted above, other factors affecting the stiffness of the tubular structure include strand diameter, strand material, and the use of a substrate such as polymer or polymer tubing that may be incorporated into the tubular structure.

Figure 5A:
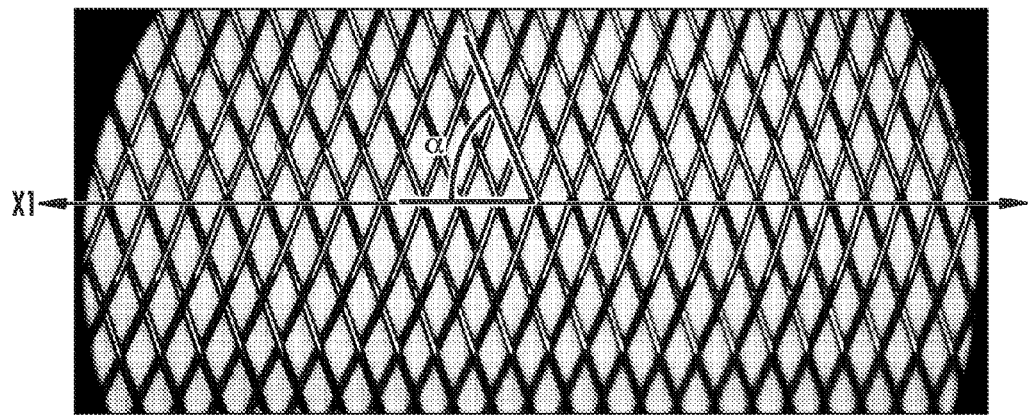
FIG. 5A is an illustration of a braid pattern with an angle α of approximately 70°.
Figure 5B:
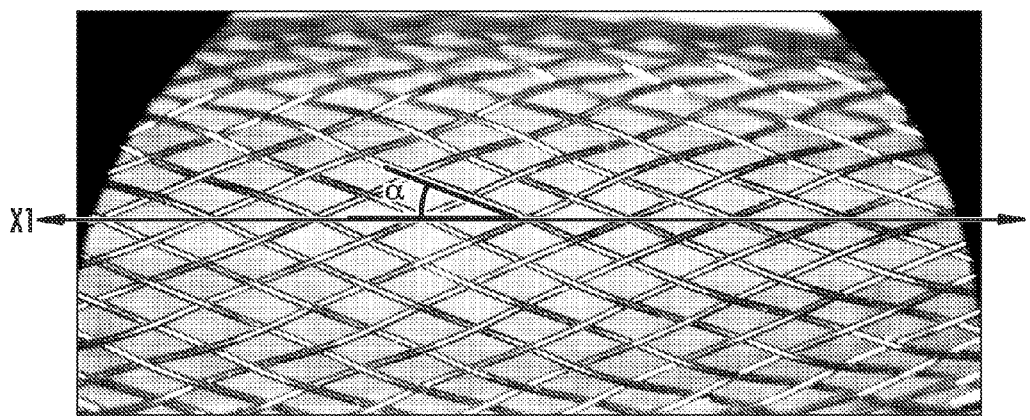
FIG. 5B is an illustration of a braid pattern with an angle α of approximately 30°.

Similarly, the angle of the strands with respect to the axis X may be varied in a "straight" braid pattern (no wave) to provide for different properties of the resulting tubular structure. The angle may range, for example, from approximately 30° to approximately 85° with respect to the longitudinal axis of the tubular structure, with smaller angles resulting from faster movement of the mandrel 30 along the axis X (or slower rotational movement of the spools) and larger angles resulting from slower movement of the mandrel along the axis (or faster rotational movement of the spools). An example of a braid pattern with an angle α of approximately 85° is shown in FIG. 5A, and an example of a braid pattern with an angle α of approximately 30° is shown in FIG. 5B. The angle may affect the stiffness of the resulting tubular structure, with smaller angles resulting in more flexible tubular structures. In the context of a wave pattern, the angle is continually changing as a result of the wave pattern, as seen in a comparison of FIG. 6 with FIGS. 5A and 5B.

Referring again to FIGS. 2A and 2B, to promote the radial strength, collapse resistance, torque transmission, column strength, and kink resistance of the resulting tubular structure, the mandrel 30 may be rotated as the first and second sets of strands are being braided onto the mandrel. In some embodiments, the mandrel 30 may be rotated about the axis X (depicted by the arrow R1 in FIG. 2A). The mandrel 30 may be rotated in one direction, or, as depicted in FIG. 7A, the mandrel may be angularly oscillated (i.e., alternately rotated in two directions) to create a braid pattern that includes crests 105 and troughs 110 (i.e., a wave pattern) with respect to the longitudinal axis X1 of the tubular structure 100, illustrated in FIG. 6. The wave pattern may, for example, for example, include one or more sinusoidal waves, sawtooth waves, square waves, and/or combinations of the same along a length of the tubular structure.

The mandrel 30 may be rotated in one direction (e.g., clockwise) to a maximum angle θ, then the direction of rotation may change and the mandrel may be rotated in the opposite direction (e.g., counterclockwise) to a maximum angle −θ (the negative sign indicating rotation in the opposite direction). The mandrel may thus be alternately rotated by an angle of θ and −θ, as illustrated in FIG. 7A, such that a point a on the surface of the mandrel travels between points b and c as the mandrel is angularly oscillated, resulting in a braid pattern such as the pattern shown in FIG. 6. It is noted that the wave line shown in FIG. 6 is merely a representation of the wave pattern created by the strand cross-over points, and not the strand itself.

The mandrel 30 (which may, for example, be a metal or polymer mandrel) may be rotated by one or more belts or drive wheels rotating reciprocally against the mandrel prior to the point at which the strands are wrapped in a braided configuration against the mandrel. The rotation may also be performed by rotating in reciprocating fashion the entire mandrel spool take-off and mandrel take-up reel assemblies relative to the braiding machine. For a short mandrel and a short braid length, however, it may be easier to couple a controllable rotational drive mechanism directly to the mandrel. Any number of other variations and methods of rotation may be used as well, so long as the desired braid pattern is achieved.

In other embodiments, the mandrel 30 may be rotated about a transverse axis (i.e., an axis that is substantially perpendicular to the longitudinal axis) to create the wave pattern. As depicted in FIG. 2B, for example, the mandrel 30 may be rotated about the transverse axis Z1 to create the wave pattern. In the embodiment of FIG. 2B, for instance, rotation about the transverse axis Z1 results in a leading end 31 of the mandrel 30 being moved in the direction D4, i.e., up and down, while the trailing end 33 is held in place with respect to the XZ plane. In other cases, the mandrel 30 may be rotated about a transverse axis such that the trailing end 33 of the mandrel 30 may be moved in the direction D4 and the leading end 31 is held stationary with respect to the XZ plane. In still other cases, the transverse axis may be between the leading end 31 and the trailing end 33, such that both the leading and trailing ends may be moved in opposite directions D4 as the mandrel pivots about the transverse axis.

Figure 6:
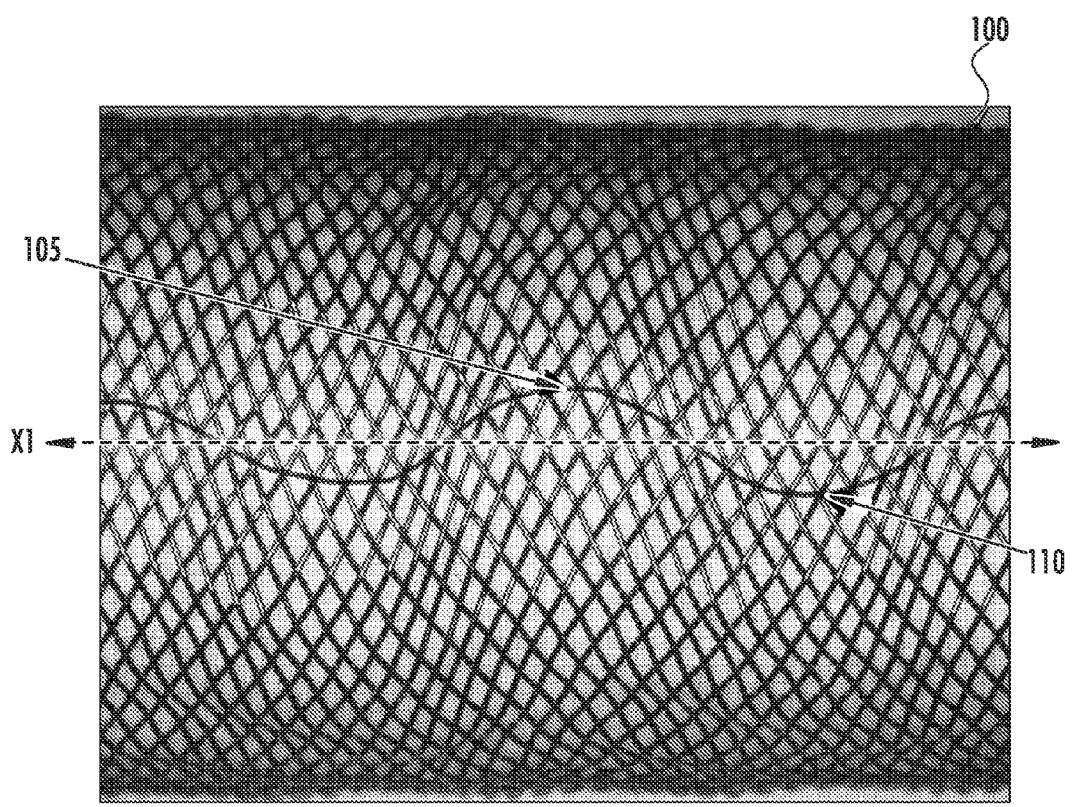
FIG. 6 depicts a braid pattern that includes crests and troughs according to an exemplary embodiment.
Figure 7A:
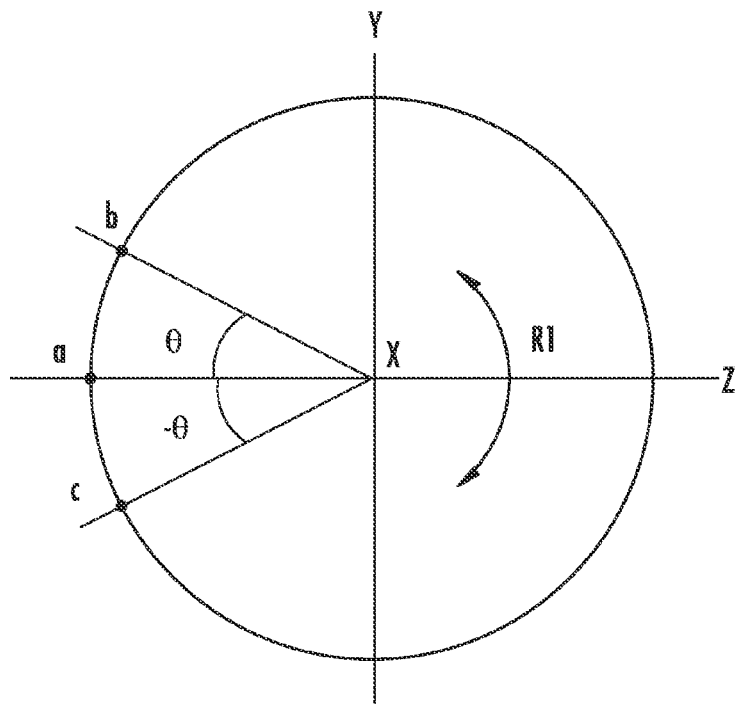
FIG. 7A is a cross-sectional view of a mandrel undergoing angular oscillations according to the exemplary embodiment of FIG. 2A.
Figure 7B:
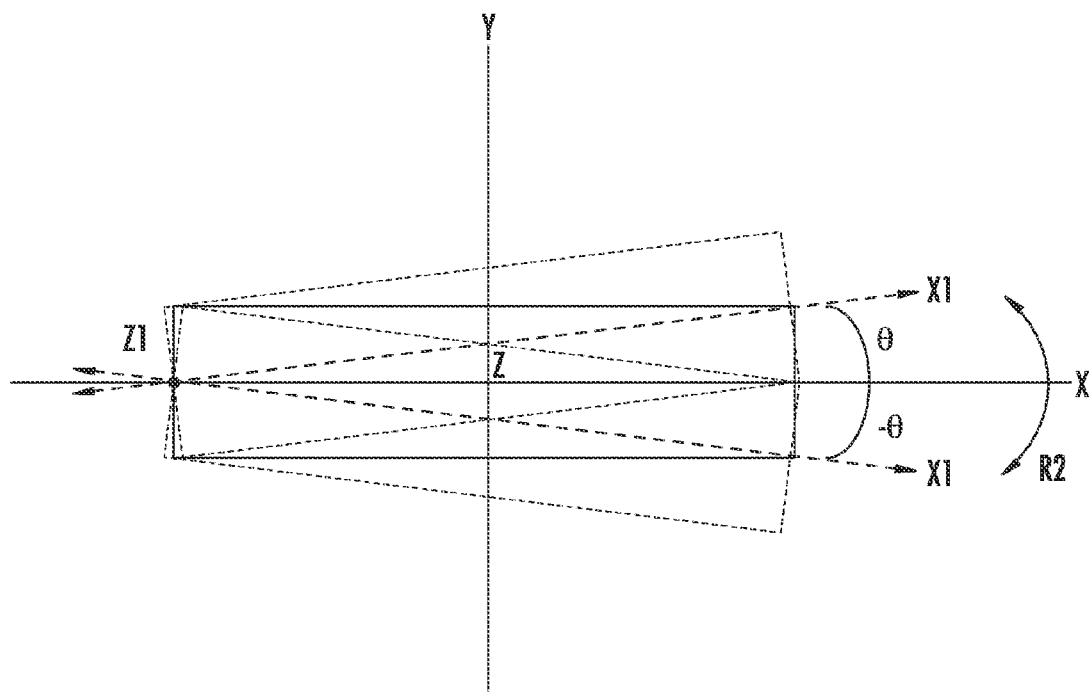
FIG. 7B is a cross-sectional view of a mandrel undergoing angular oscillations according to the exemplary embodiment of FIG. 2B.

Again, the mandrel 30 may be angularly oscillated (about the transverse axis Z1) to create a wave pattern along a length of the tubular structure 100, shown in FIG. 6. As illustrated in FIG. 7B, the mandrel 30 may be rotated in one direction (e.g., up) to a maximum angle θ, then the direction of rotation may change and the mandrel may be rotated in the opposite direction (e.g., down) to a maximum angle $-\theta$ (the negative sign indicating rotation in the opposite direction). The mandrel may thus be alternately rotated by an angle of $\theta$ and $-\theta$, as shown in FIG. 7B. Alternatively, for a uniform symmetrical wave pattern about the circumference of the braid, the mandrel may be fixed at one end and moved at the other end in a circular pattern transverse to the X axis such that the mandrel surface sweeps a conical shape, with the axis of the mandrel forming an angle $\theta$ with the X axis and no mandrel rotation about the X axis. In this particular case, no reversal in direction of rotation of the mandrel would be needed.

Figure 8:
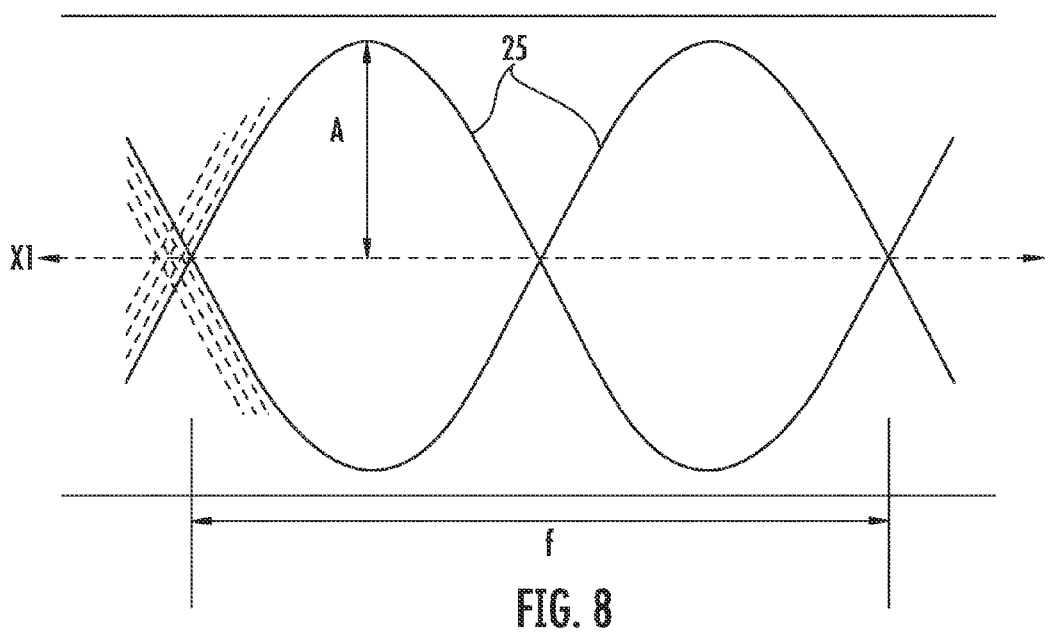
FIG. 8 depicts the amplitude and frequency of an observed wave pattern according to an exemplary embodiment.

In either case (where the mandrel is angularly oscillated about the axis X or the axis Z1), the angle through which the mandrel is rotated may correspond to the amplitude A of the wave in the resulting braid pattern, as shown in FIG. 8 (in which only a representative pathway of strand cross-over points is shown, for clarity). Thus, as the maximum angle $\theta/-\theta$ through which the mandrel is rotated is increased, the resulting amplitude A of the wave in the braid pattern also increases. Furthermore, the speed of angular oscillation corresponds to the frequency f of the waves. Thus, for a given mandrel axial speed, as the rate of angular oscillation is increased, the frequency f increases (i.e., there are more crests and troughs per unit of length along the axis X1 of the tubular structure).

Referring again to FIGS. 7A and 7B, in some cases, the maximum angle $\theta/-\theta$ through which the mandrel rotates may be varied such that the mandrel is rotated to a first maximum angle $\theta 1$ in a first direction (e.g., clockwise) and to a second maximum angle $\theta 2$ in a second direction (e.g., counterclockwise), the magnitude of the second maximum angle being different from the magnitude of the first maximum angle. For example, in the case of angular oscillations about the longitudinal axis X (FIG. 7A), the mandrel may be rotated in the clockwise direction to a maximum angle of 30° and in the counterclockwise direction to a maximum angle of 45°. As a result, the mandrel may continually be rotated in the counterclockwise direction (in this example), imparting certain torsional characteristics to the resulting tubular structure, such as to provide a torque response or other property more favorable in one direction than another. In the case of rotation about the transverse axis Z1 (FIG. 7B), the mandrel may be rotated in a first direction by a first angle (e.g., 15°), in a second direction by a second angle (e.g., 13°) then again in the first direction by a third angle (e.g., 11°), etc., with decreasing angles $\theta$ of rotation. In this example, the resulting wave pattern may exhibit waves with decreasing amplitudes, gradually becoming a "straight" braid pattern (i.e., no waves).

Aside from rotating the mandrel, still other methods of imparting a wave pattern to the braid may include changing the speed at which the spool carriers 35 rotate (depicted in FIG. 3 by the arrows CCW and CW) while maintaining the mandrel's axial speed, or, alternatively, rotating the braiding machine 20 (e.g., shown in FIG. 2A) about the axis X in a direction depicted by the arrow R1 with respect to the mandrel 30. By rotating the braiding machine 20, for example, all of the carriers 35 are rotated at the same time, while the individual carriers or sets of carriers continue to rotate and translate to braid the strands onto the mandrel.

As noted above, the number of strands in each set, the diameter of the strands, the pic count of the braided strands, the rotational speed of the spools, and the movement of the mandrel (axially and/or angularly) may be adjusted as desired to produce a particular braid configuration for a particular application. In addition, the material of the strands and the type of braiding (one over one, two over one, etc.) may also be selected to produce desirable characteristics in the tubular structure.

In this regard, the strands may be comprised of any material, such as natural materials, polymers, metals, or metallic alloys. In some applications, wire strands may be used. The wire strands may be formed of a material that is both resilient and can be heat treated to stabilize the tubular structure (e.g., to substantially set a desired shape or braid pattern). In some cases, at least some of the strands include at least one metal, such as steel, stainless steel, shape memory alloy, pseudo-elastic alloy, and elastic alloy.

With respect to medical devices, where it is important for the device to be delivered to a target site in the body in a reduced profile configuration and subsequently allowed to self-expand after being released from the constraint, stainless steel, other metallic alloys, highly elastic alloys, and/or shape memory alloys may be used that are both resilient and can be heat treated to substantially set a desired shape. Exemplary suitable materials may include, for example, cobalt-based low thermal expansion alloys referred to as Elgiloy® Co—Cr—Ni alloy, nickel-based high temperature high-strength "superalloys" (for example, alloys commercially available from Haynes International under the trade name Hastelloy® alloy), nickel-based heat treatable alloys (for example, alloys commercially available from International Nickel under the trade name Incoloy® alloy) and a number of different grades of stainless steel.

In some embodiments, a factor in choosing a suitable material for the strands is the ability of the strands to retain a suitable amount of the deformation induced by the molding surface when subjected to a predetermined heat treatment, such as is exhibited by shape-memory alloys. One type of shape memory alloy is nickel-titanium (NiTi) alloy, called Nitinol alloy, which is also very elastic. In stent-graft applications, for example, this elasticity may allow a self-expanding stent-graft to return to a preset expanded configuration from a contracted configuration once it is deployed from a delivery catheter and is no longer constrained. Accordingly, in some embodiments, at least some of the strands comprise a shape memory alloy such that the resulting tubular structure is configured to have an expanded configuration when the tubular structure is not constrained (radially or axially) and to have a collapsed configuration when the tubular structure is constrained. In this way, the tubular structure may be configured to self-expand from the collapsed configuration to the expanded configuration when an applied constraint (such as a sheath inside of which the stent-graft is disposed in the collapsed configuration) is removed. Other materials having elastic properties may also be used, such as spring stainless steel and alloys such as Elgiloy®, Hastelloy®, Phynox®, MP35N®, and CoCrMo alloys.

In some instances, polymeric materials may also be used for the strands. Furthermore, polymeric materials may be combined with other materials in the formation of tubular structures for certain applications. For example, for catheter shaft tubing (e.g., for balloon catheters or stent delivery systems), the tubular structure may include a combination of polyamide tubing and stainless steel wire. In other cases, materials may be used that are compatible with magnetic resonance imaging (MRI), considering that some materials may generate heat or experience torque as a result of undergoing MRI or may distort the MRI image. Thus, metallic and/or non-metallic materials that reduce or eliminate the potential problems resulting from the use of MRI may be used, depending on the application.

In some embodiments, as few as 8 strands and as many as 288 strands (and possibly more) may be used to make the braid pattern of the tubular structure. The strands may be braided onto a mandrel ranging from approximately 3 mm to approximately 40 mm in diameter. For example, a tubular structure intended for use as a medical device may be made by braiding 144 strands onto a 4 mm mandrel.

According to one embodiment, in which a tubular structure is used for a medical device, each of the first and second sets of strands for braiding the tubular structure may include 36 to 144 strands. For example, each layer of the tubular structure may comprise 36 strands having a diameter of from about 0.0010 to about 0.0100 inches, with the diameter of the strands dependent upon the performance requirements for the device and where in the body the device will be positioned. For example, a device used to treat an atrial septal defect in an adult may have a strand diameter of approximately 0.008 inches, whereas a device used to treat a patent ductus arteriosis in a child may have a strand diameter of 0.00125 inches.

The strands may include a shape memory alloy, such as Nitinol, and may be braided so as to define fenestrations with an area of about 0.00015 sq. in. to about 0.0030 sq. in. that are sufficiently small so as to slow the blood flow through the wall of the device and facilitate thrombus formation thereon Inner and outer braided layers may be braided (e.g., having a particular pic count, strand diameter, number of strands, etc.) so as to obtain desirable collapse and expansion characteristics, such as for maintaining a uniform overall length of the device. As noted above, the tubular structure may include multiple layers of braided strands as a result of braiding the first and second sets of strands onto the mandrel in multiple layers (e.g., braiding a first layer, then resetting the mandrel and braiding a second layer over the top of the first layer with the mandrel moving in the same axial direction as the strands are braided).

Once the tubular structure has been braided onto the mandrel as described above, the tubular structure may undergo further processing to prepare the tubular structure or a portion of the tubular structure for use in a particular device or application. For example, a medical device (such as the stent-graft 10 depicted in FIG. 1) may be made by cutting an appropriately sized portion from a tubular structure, as described above. When cutting the fabric to the desired dimensions, one may solder, braze, weld, coat, glue, clamp, tie, or otherwise affix the ends of the cut portion together to minimize the risk of unraveling the braid pattern.

Once an appropriately sized piece of the fabric is obtained, the fabric may be deformed to generally conform to a surface of a molding element. Deforming the fabric may reorient the relative positions of the braided strands from their original order to a second, reoriented configuration; however, the braid pattern of crests and troughs should be generally maintained. To minimize any undesirable changes to the braid pattern during significant shape forming, the braid may be stabilized by heat setting the braid pattern on the mandrel or removing the tubular structure from the mandrel and heat setting the braid pattern prior to shape forming into the mold. This may help to substantially lock in the braid pattern while allowing the relative wire reorientation to achieve the shape formation of the mold. In other cases, however, heat setting may not be necessary, as the wave pattern itself may be self-locking.

The shape of the molding element should be selected to deform the fabric into substantially the desired shape. In medical device applications, for example, the shape of the molding element may be selected to deform the tubular structure into substantially the shape of the desired medical device when unconstrained (e.g., deployed from a delivery device). Once the molding element is assembled with the fabric generally conforming to a molding surface of that element, the fabric can be subjected to a heat treatment while it is maintained in contact with that molding surface. For example, suitable heat treatments of Nitinol wire to set a desired shape are well known in the art. It has been found that holding a Nitinol fabric at about 500° C. to about 550° C. for a period of about 1 to about 30 minutes, depending on the softness or harness of the device to be made, will tend to set the fabric in its deformed state, such that the fabric conforms to the molding surface of the molding element. At lower temperatures the heat treatment time will tend to be greater (e.g., about one hour at about 350° C.), and at higher temperatures the time will tend to be shorter (e.g., about 30 seconds at about 900° C.).

In some cases, the tubular structure may be braided over one or more layers of thin polymer extrusions, followed by application of a polymer extrusion or other coating or adhesive over the braid that serves to stabilize the braid pattern (e.g., instead of or in addition to heat treatment). Alternatively an adhesive or binder may be placed over the mandrel before braiding to stabilize the braid as it is being braided onto the mandrel. As another alternative, a separate polymer sleeve may be heat shrunk or heat pressed into the braid pattern to lock the braid. In still other cases, the braid pattern of the tubular structure may not need to be stabilized at all.

In some cases, other types of coverings may be applied to a surface of the braided strands. For example, in medical device applications, the braided strands may be coated with a suitable thrombogenic or anti-thrombogenic agent or with a drug. In some instances, the tubular structure may be covered or filled with a polyester fiber, polymer fiber, or animal tissue portion, or the tubular structure may be braided with an increased number of wire strands to speed up the occlusion of the vessel. For example, the occluding portion that is incorporated in the tubular structure may be configured to allow blood to be caught in the interwoven fiber and form a clot that is retained firmly within the device as it forms the occlusion.

The tubular structure may be braided to include a plurality of planes of occlusion. A plane of occlusion may be any surface, whether flat or irregular in shape, that may be oriented at least partially transverse to the flow of blood so as to facilitate the formation of thrombus. At least one plane of occlusion may include one or more layers of occlusive material, such as a layer of fabric and/or a layer of polyester fiber and/or a layer of metal, two layers of metal, or two layers of polyester. Thus, the tubular structure may include one or more polymer or metal layers. For example, a stent-graft may have one layer of metal acting as a plane of occlusion. By modifying the configuration of the tubular structure, the number of planes of occlusion may be modified. Alternatively, by changing the number of layers of occlusive material, the rate at which the medical device occludes a vascular abnormality may also be modified.

The above embodiments provide for a number of advantages in the tubular structure. For example, the resulting tubular structure generally has greater strength than a structure braided without the wave pattern of the described embodiments. As noted above, such improvements in strength include increased radial strength, kink resistance, collapse resistance, pushability, stiffness, and/or other strength characteristics. As a result, fewer strands and/or smaller diameter strands may be used to form tubular structures with the desired properties with resultant thinner walls or a lower profile, as compared to structures formed in a manner not in accordance with the described embodiments or having more strands or larger diameter strands.

In medical devices such as self-expanding stent-grafts, there may be a trade-off between the draw down of the tubular structure (i.e., the minimum diameter of the stent-graft in the contracted state, upon being pulled axially for delivery through a catheter) and the increased strength of the structure in its expanded state due to having braided strands exhibiting a braid pattern including crests and troughs in accordance with the embodiments described above. For example, although increasing the relative size and frequency of the crests and troughs may increase the strength of the tubular structure, it may not be physically possible to decrease the diameter of the structure in the contracted state below a certain point. Thus, an appropriate amplitude and frequency of the wave pattern may be selected to provide the desired strength while providing an adequate amount of flexibility for the structure.

Numerous advantages may be gained from the increased strength of the tubular structure as compared to a structure having the same braided strands but no wave pattern. In tubing having portions with different diameters, tubular structures exhibiting a braid pattern with crests and troughs, as described above, may have improved stiffness, radial strength, collapse resistance, kink resistance, and other properties in select portions of the tubing. In some cases, tubular structures with braided wave patterns in accordance with the embodiments described above may be useful for multilayer devices, such as three-dimensional braided structures.

The tubular structure may be braided such that the whole device exhibits the same wave pattern, or only portions of the device exhibit the wave pattern (with other portions having a different wave pattern or no wave pattern at all, as detailed herein). Wave patterns in the braided strands in accordance with the embodiments described above may improve torque response from one end of the tubular structure to the other end. For example, a tubular structure may be braided that exhibits a wave pattern at each end of the structure and no wave pattern at all in the middle portion. In this way, the torque response may be decreased in the middle portion (where there is no wave). Thus, while the wave pattern at each end may act as an anchor within the patient's vessel, the no-wave portion in the middle may be free to bend and twist as required, such as for use in a patient's Popliteal vessels.

Also, occlusion properties may be locally varied, such as for treating a side aneurysm in a vessel, by increasing the strand density adjacent the opening of the aneurysm via increasing the pic count or wave pattern frequency. In some cases, wave patterns may also be used to achieve desired axial column strength or pushability in one or more sections of a shaft or tubing, thereby locally varying the strength properties of the tubular structure. Thus, in medical devices such as stent-grafts, the kink resistance of tubular structure in particular sections or the whole device may be improved, which may be particularly useful when the device is employed in locations subject to bending forces, such as in arteries that pass through the knee or through other joints or in superficial femoral arteries.

As noted above, various parameters of the braiding operation may be manipulated to achieve a tubular structure with desired characteristic. As an example, the following parameters may be applied to a braiding operation to produce a tubular structure having braided strands that exhibit a braid pattern including crests and troughs with respect to a longitudinal axis of the tubular structure (e.g., a tubular structure that exhibits a wave pattern along a length of the structure) that possesses desired properties for use in a medical device:

(i) the mandrel may have a diameter of 9 mm;
(ii) the first and second sets of strands may each include 36 spools providing 36 strands;
(iii) the strand material may be Nitinol wire with a diameter of approximately 0.0035 inches; and
(iv) the pics per inch (i.e., wire strand crossings per inch of braided strands) may be set to 66 pics per inch (PPI).

In addition, in the example detailed above, the braided tubular structure may be pre-baked to a heat setting of approximately 425° C. and then may be heat set to approximately 500° C. in a 600° C.-capable oven in the desired final shape of the device.

Several examples of resulting braid patterns are shown in FIGS. 9-13. These structures are generated using embodiments of the above-described methods. In an exemplary embodiment, the depicted structures are created on a straight mandrel in segments. As illustrated, the resulting braid patterns exhibited by the tubular structures may have different amplitudes and frequencies to promote different characteristics in the tubular structures. For example, the braid patterns shown in FIGS. 10-13 differ from the braid pattern in FIG. 9 and from one another in the respective amplitudes and frequencies of the braided crests and troughs. The amplitudes and frequencies are directly related to the oscillation methods used to generate them, as described above with respect to FIGS. 7A and 7B.

Figure 9:
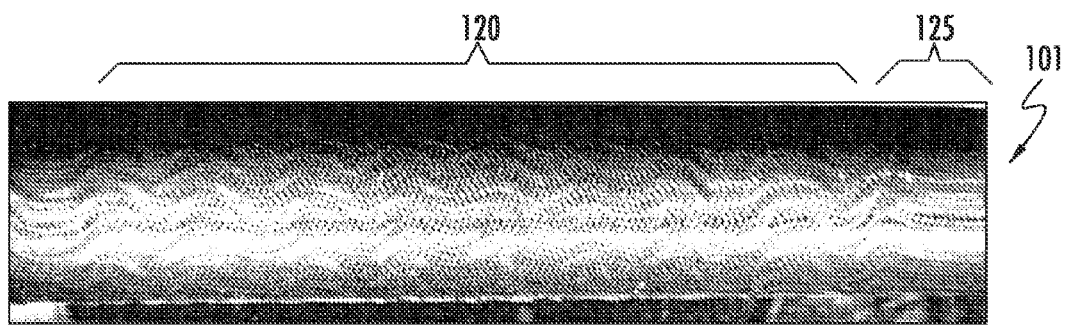
FIGS. 9-13 are representations of braid patterns of tubular structures according to exemplary embodiments.
Figure 10:
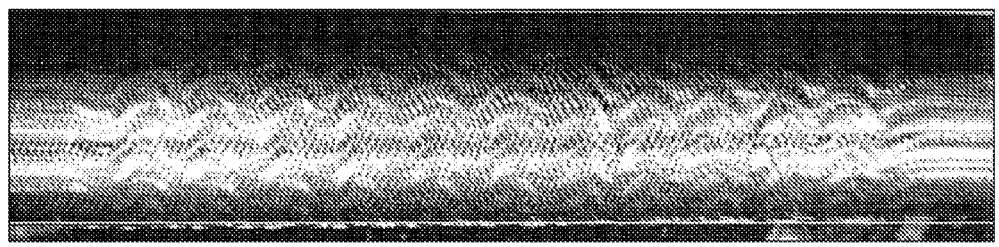
Figure 11:
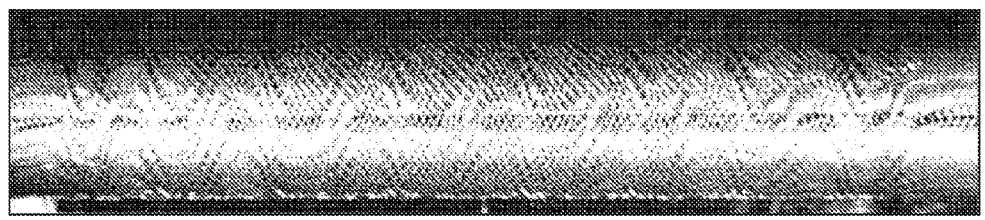
Figure 12:
Figure 13:
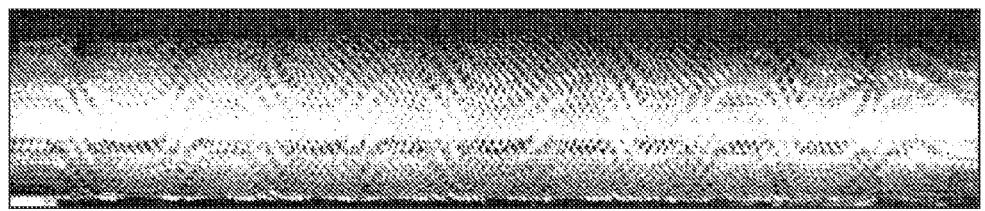

In addition, factors such as the speed of angular oscillation and the maximum angle through which the mandrel is rotated may be changed or varied as the strands are braided onto the mandrel, resulting in a tubular structure in which the braided strands exhibit a first braid pattern in one portion of the tubular structure and a second, different braid pattern in another portion of the tubular structure. In FIG. 9, for example, the resulting tubular structure 101 exhibits a first braid pattern 120 that includes crests and troughs (i.e., a wave pattern) in one portion of the tubular structure and a second braid pattern 125 that does not include crests and troughs but, rather, is linear in another portion of the tubular structure. In other cases, one portion of the tubular structure may exhibit a first braid pattern having a particular amplitude and/or frequency, whereas another portion of the tubular structure may exhibit a second braid pattern having a different amplitude and/or frequency. In this way, the resulting tubular structure may have varying local properties, depending on the braid pattern used in a certain area of the tubular structure. For example, sections of the stent-graft that abut a target site or need to have increased radial strength (e.g., due to greater pressure in a certain area where the device is placed) may be braided to have a wave pattern with a higher amplitude and/or a shorter frequency to provide enhanced strength properties, whereas other sections of the tubular structure (e.g., sections where increased radial strength is not required, such as the ends of the device or portions of the device placed in low-stress areas) may have a different wave pattern, or no wave pattern at all.

Figure 14:
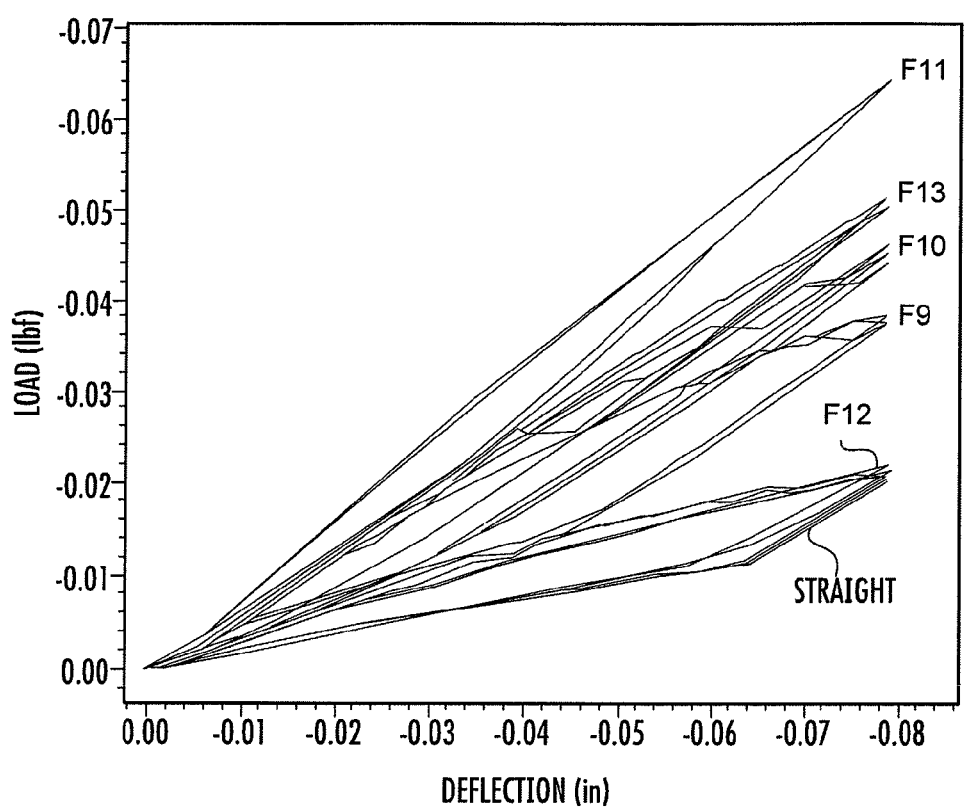
FIG. 14 illustrates an empirical analysis of the radial compressive strength of each of the tubular structures depicted in FIGS. 9-13.

FIG. 14 illustrates an empirical analysis of the radial compressive strength of each of the tubular structures depicted in FIGS. 9-13 (labeled "F9," "F10," "F11," "F12," and "F13" in the figure). To test the compressive strength of each tubular structure, a sample length of the tubular structure was placed horizontally between two horizontal plates. The top plate had a flat surface for applying a load to the tubular structure, whereas the bottom plate included a slight curvature to hold the tubular structure in place. The top plate was moved downward at a set rate to compress the sample to a preset defection and then moved back upward to its starting point. As the top plate moved, the resulting force on the tubular structure was measured with the greatest force occurring at the maximum deflection. FIG. 14 shows the load force as a result of the applied deflection for each of the tubular structures depicted in FIGS. 9-13. In other words, FIG. 14 shows the radial force for each of the samples tested as depicted in FIGS. 9-13, as well as a "straight" sample (i.e., a tubular structure made using the same braiding parameter, but not including a wave pattern, labeled "STRAIGHT").

As demonstrated, larger amplitude waves typically result in a higher radial strength than smaller amplitude waves with the same given frequency. Alternately, a wave pattern with a shorter frequency (more waves per unit length) typically results in a higher radial strength than one with a longer frequency (fewer waves per unit length), where the waves have the same given amplitude. Consequently, various combinations exist, and a combination of the largest amplitude and shortest frequency waves should yield the highest radial strength. Conversely, a combination of smaller amplitude and longer frequency waves should yield a lower radial strength, as demonstrated in FIG. 14 by the similar radial strength results achieved by the sample corresponding to the braid pattern depicted in FIG. 12 and a "straight" braid pattern.

This invention has been described herein in considerable detail in order to comply with the Patent Statutes and to provide those skilled in the art with the information needed to apply the novel principles and to construct and use embodiments of the example as required. However, it is to be understood that specifically different devices can carry out the invention and that various modifications can be accomplished without departing from the scope of the invention itself. For example, options shown for one embodiment could easily be applied to other embodiments, as desired for a particular application, without departing from the scope of this invention.

That which is claimed:

1. A method of braiding a plurality of strands into a tubular structure comprising:
    braiding at least a first set of strands and at least a second set of strands onto a mandrel;
    moving the mandrel along a longitudinal axis of the mandrel as the first and second sets of strands are being braided onto the mandrel; and
    rotating the mandrel as the first and second sets of strands are being braided onto the mandrel such that at least a portion of the braided strands exhibit a wave pattern that includes crests and troughs along a length of the tubular structure.

2. The method of claim 1, wherein rotating the mandrel comprises rotating the mandrel about the longitudinal axis.

3. The method of claim 1, wherein rotating the mandrel comprises rotating the mandrel about a transverse axis that is substantially perpendicular to the longitudinal axis.

4. The method of claim 1, wherein braiding the first and second sets of strands onto the mandrel comprises rotating the first set of strands in a first direction about the longitudinal axis and rotating the second set of strands in a second direction about the longitudinal axis.

5. The method of claim 1, wherein each strand extends from a spool to the mandrel, and wherein braiding the first and second sets of strands onto the mandrel comprises rotating the spools of the first set of strands in a first direction about the longitudinal axis, rotating the spools of the second set of strands in a second direction about the longitudinal axis, and translating the spools of the first set of strands and the spools of the second set of strands radially with respect to the longitudinal axis.

6. The method of claim 1 further comprising:
    changing a speed of the braiding of the first and second sets of strands or changing a speed of the movement of the mandrel along the longitudinal axis as the first and second sets of strands are being braided onto the mandrel to vary a pic count of a resulting braid pattern.

7. The method of claim 1 further comprising:
    applying a first braid pattern to a first portion of the tubular structure and applying a second braid pattern to a second portion of the tubular structure, wherein the first braid pattern is different from the second braid pattern.

8. The method of claim 1 further comprising:
    stabilizing a braid pattern of the tubular structure by heat setting the braid pattern.

9. The method of claim 1 further comprising:
    applying a covering to an exterior surface of at least a portion of the tubular structure.

10. The method of claim 1 further comprising:
    stabilizing a braid pattern of the tubular structure by braiding the first and second sets of strands onto at least one polymer layer.

11. The method of claim 10 further comprising:
    applying a covering to an exterior surface of at least a portion of the tubular structure.

12. The method of claim 1, wherein rotating the mandrel comprises angularly oscillating the mandrel.

13. The method of claim 12 further comprising:
    changing a speed of the angular oscillation.

14. The method of claim 1 further comprising:
    varying a maximum angle through which the mandrel rotates.

15. The method of claim 14, wherein varying the maximum angle comprises:
    rotating the mandrel to a first maximum angle in a first direction; and
    rotating the mandrel to a second maximum angle in a second direction, wherein a magnitude of the second maximum angle is different from a magnitude of the first maximum angle.

16. The method of claim 1, wherein braiding the first and second sets of strands comprises braiding the first and second sets of strands onto the mandrel in multiple layers.

17. A method of braiding a plurality of strands into a tubular structure comprising:
    braiding a first set of strands extending from first spools and a second set of strands extending from second spools onto a mandrel, the step of braiding including:
        rotating the first spools in a first direction about a longitudinal axis of the mandrel;
        rotating the second spools in a second direction about the longitudinal axis; and
        translating the first and second spools radially with respect to the longitudinal axis;
    moving the mandrel along the longitudinal axis as the first and second sets of strands are being braided onto the mandrel; and
    rotating the mandrel as the first and second sets of strands are being braided onto the mandrel.

18. The method of claim 17, wherein the step of rotating the mandrel as the first and second sets of strands are being braided onto the mandrel results in at least a portion of the braided strands exhibiting a wave pattern that includes crests and troughs along a length of the tubular structure.

19. The method of claim 17 further comprising:
    changing a speed of the braiding of the first and second sets of strands or changing a speed of the movement of the mandrel along the longitudinal axis as the first and second sets of strands are being braided onto the mandrel to vary a pie count of a resulting braid pattern.

20. The method of claim 17 further comprising:
applying a first braid pattern to a first portion of the tubular structure and applying a second braid pattern to a second portion of the tubular structure, wherein the first braid pattern is different from the second braid pattern.

21. The method of claim 20, wherein at least one of the first and second braid patterns is a wave pattern.

22. The method of claim 17 further comprising:
stabilizing a braid pattern of the tubular structure by heat setting the braid pattern or by braiding the first and second sets of strands onto at least one polymer layer.

23. The method of claim 17 further comprising:
applying a covering to an exterior surface of at least a portion of the tubular structure.

24. The method of claim 17 further comprising:
varying a maximum angle through which the mandrel rotates, wherein varying the maximum angle comprises rotating the mandrel to a first maximum angle in a first direction and rotating the mandrel to a second maximum angle in a second direction, a magnitude of the second maximum angle being different from a magnitude of the first maximum angle.

25. The method of claim 17, wherein the step of braiding the first and second sets of strands comprises braiding the first and second sets of strands onto the mandrel in multiple layers.

26. A method of braiding a plurality of strands into a tubular structure comprising:
braiding a first set of strands and a second set of strands onto a mandrel;
moving the mandrel along a longitudinal axis of the mandrel as the first and second sets of strands are being braided onto the mandrel; and
rotating the mandrel as the first and second sets of strands are being braided onto the mandrel by angularly oscillating the mandrel.

27. The method of claim 26 further comprising:
changing a speed of the angular oscillation.

28. The method of claim 26, wherein the step of rotating the mandrel as the first and second sets of strands are being braided onto the mandrel results in at least a portion of the braided strands exhibiting a wave pattern that includes crests and troughs along a length of the tubular structure.

29. The method of claim 26, wherein the step of braiding the first and second sets of strands onto the mandrel comprises:
rotating the first set of strands in a first direction about the longitudinal axis; and
rotating the second set of strands in a second direction about the longitudinal axis.

30. The method of claim 26 further comprising:
changing a speed of the braiding of the first and second sets of strands or changing a speed of the movement of the mandrel along the longitudinal axis as the first and second sets of strands are being braided onto the mandrel to vary a pic count of a resulting braid pattern.

31. The method of claim 26 further comprising:
applying a first braid pattern to a first portion of the tubular structure and applying a second braid pattern to a second portion of the tubular structure, wherein the first braid pattern is different from the second braid pattern.

32. The method of claim 26 further comprising stabilizing a braid pattern of the tubular structure by heat setting the braid pattern or by braiding the first and second sets of strands onto at least one polymer layer.

33. The method of claim 26 further comprising:
varying a maximum angle through which the mandrel rotates, wherein varying the maximum angle comprises rotating the mandrel to a first maximum angle in a first direction and rotating the mandrel to a second maximum angle in a second direction, a magnitude of the second maximum angle being different from a magnitude of the first maximum angle.

34. The method of claim 26, wherein the step of braiding the first and second sets of strands comprises braiding the first and second sets of strands onto the mandrel in multiple layers.

35. The method of claim 26 further comprising:
applying a covering to an exterior surface of at least a portion of the tubular structure.

\* \* \* \* \*

UNITED STATES PATENT AND TRADEMARK OFFICE
CERTIFICATE OF CORRECTION

| | |
|---|---|
| PATENT NO. | : 8,511,214 B2 |
| APPLICATION NO. | : 13/091763 |
| DATED | : August 20, 2013 |
| INVENTOR(S) | : Gries |

It is certified that error appears in the above-identified patent and that said Letters Patent is hereby corrected as shown below:

In the Claims

Column 19,
Line 2, "pie count" should read --pic count--.

Signed and Sealed this
Twenty-second Day of October, 2013

Teresa Stanek Rea
*Deputy Director of the United States Patent and Trademark Office*